United States Patent
Iwakura et al.

(10) Patent No.: US 6,566,532 B2
(45) Date of Patent: May 20, 2003

(54) PROCESS FOR PRODUCING OPTICALLY ACTIVE HEMIESTERS

(75) Inventors: Kazunori Iwakura, Ibaraki; Hiroshi Souda, Takatsuki, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/779,848

(22) Filed: Feb. 9, 2001

(65) Prior Publication Data

US 2001/0023302 A1 Sep. 20, 2001

(30) Foreign Application Priority Data

Feb. 9, 2000  (JP) ........................ 2000-031798
Feb. 10, 2000 (JP) ........................ 2000-033295

(51) Int. Cl.$^7$ ............................ C07D 233/02

(52) U.S. Cl. ................. 548/316.4; 548/316.7

(58) Field of Search ............. 548/316.4, 316.7

(56) References Cited

U.S. PATENT DOCUMENTS

| 4,687,859 A | 8/1987 | Pauling et al. |
| 2002/0038048 A1 | 3/2002 | Deng et al. |

FOREIGN PATENT DOCUMENTS

| EP | 0044158 | * | 1/1982 |
| EP | 0084892 | * | 3/1983 |
| EP | 0092194 | * | 10/1983 |
| EP | 0 161 580 B1 | | 11/1985 |
| WO | 01/74741 A2 | | 10/2001 |

OTHER PUBLICATIONS

Seebach, et al., Highly Enantioselective Opening of Cyclic . . . , *Communications*, Angew. Chem. Int. Ed. Engl. 1995, vol. 34, No. 21, pp. 2395–2396.
Seebach, et al., Resolution of Racemic Carboxylic Acid . . . , *Tetrahedron*, vol. 53, No. 22, 1997, pp. 7539–7556.
Jaeschke, et al., Highly Enantioselective Ring Opening . . . , *J. Org. Chem.*, vol. 63, 1998, pp. 1190–1197.
Aitken, et al., Catalytic Asymmetric Synthesis of Highly . . . , *J. Chem. Soc., Chem. Commun.*, 1988, 632–634.
Aitken, et al., Catalytic Asymmetric Ring–Opening . . . , *Tetrahedron: Asymmetry*, vol. 1, No. 8, 1990, pp. 517–520.
Shimizu, et al., Enantioselective Esterification of Cyclic Dicarboxylic . . . , *Bull. Chem. Soc. Jpn.*, vol. 66, No. 7, pp. 2128–2130, 1993.
Hiratake, et al., Catalytic Asymmetric Induction from Prochiral . . . , *J. Chem. Soc. Chem. Commun.*, 1985, pp. 1717–1719.
Hiratake, et al., Enantiotopic–group Differentiation . . . , *J. Chem. Soc. Perkin Trans.*, vol. 1, 1987, pp. 1053–1058.
Bernardi, et al., Improved synthesis of both enantiomers . . . , *Tetrahedron: Asymmetry*, vol. 10, 1999, pp. 3403–3407.
Bolm, et al., Simple and Highly Enantioselective . . . , *Synlett*, No. 2, 1999, pp. 195–196.
Bolm, et al., Practical and Highly Enantioselective Ring . . . , *J. Org. Chem.*, vol. 65, 2000, pp. 6984–6991.

* cited by examiner

Primary Examiner—Joseph K. McKane
Assistant Examiner—Golam M. M. Shameem
(74) Attorney, Agent, or Firm—Birch, Stewart, Kolasch & Birch, LLP

(57) ABSTRACT

There is disclosed a process for producing an optically active hemiester of formula (1):

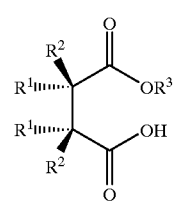

(1)

wherein $R^1$, $R^2$ and $R^5$ represent the same meanings as described below, which comprises reacting a cyclic acid anhydride of formula (2):

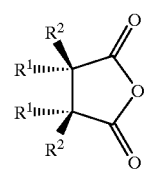

(2)

wherein $R^1$ and $R^2$ are different and independently represent a hydrogen atom, a halogen atom, an alkyl group optionally substituted with an alkoxy group or a halogen atom, and the like, with a hydroxy compound of formula (3):

$R^3OH$ (3)

wherein $R^3$ represents an alkyl group optionally substituted with an alkoxy group, a phenoxy group, a dialkylamino group or a halogen atom and the like, in the presence of an asymmetric catalyst.

8 Claims, No Drawings

PROCESS FOR PRODUCING OPTICALLY ACTIVE HEMIESTERS

FIELD OF THE INVENTION

The present invention relates to a process for producing an optically active hemiester.

BACKGROUND OF THE INVENTION

An optically active hemiester, for example, an imidazolidin 2-one hemiester derivative has been known as an intermediate for synthesizing d-biotin (vitamin H) and the like. There have been known a process for producing hemiester intermediate derivatives by ring-opening reactions of a cyclic acid anhydride using a complex of alkaloids and dialkylzinc as described in Bull. Chem. Soc. Jpn, 1993, 66, 2128, and a process of using an optically active diisopropoxytitanium TADDOLate as described in J. Org. Chem, 1998, 63, 1190.

SUMMARY OF THE INVENTION

According to the present invention, an optically active hemiester with good optical activity can be industrially advantageously obtained.

The first aspect of the present invention relates to a process for producing an optically active hemiester of formula (1):

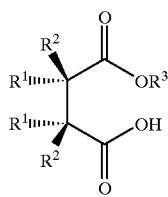

(1)

wherein $R^1$, $R^2$ and $R^3$ represent the same meanings as described below, which comprises reacting a cyclic acid anhydride of formula (2);

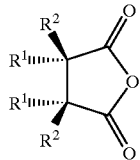

(2)

with a hydroxy compound of formula (3):

$R^3OH$ (3)

in the presence of an asymmetric catalyst comprising
a Lewis acid compound selected from a halide, alkoxide or trifluoromethanesulfonate of an element of Group 3, 4, 13 or 14 of Periodic Table of the Elements, and
an optically active ligand selected from a diol, aminoalcohol or bisoxazoline compound, wherein in formulae (1), (2) and (3) $R^1$ and $R^2$ are different and independently represent
a hydrogen atom, a halogen atom,
an alkyl group optionally substituted with an alkoxy group or a halogen atom,
an alkenyl group optionally substituted with an alkoxy group or a halogen atom,
an aralkyl group optionally substituted with an alkyl group, an alkoxy group or a halogen atom,
an aryl group optionally substituted with an alkyl group, an alkoxy group or a halogen atom, or
a group of formula(10): $R^aO-$, $R^bNH$, or $R^aR^bN$, wherein
$R^a$ represents
an alkyl group, an aralkyl group, a silyl group, or an acyl group, and
$R^b$ represents
an acyl group, an alkoxycarbonyl group, an aralkyloxycarbonyl group, an alkylsulfonyl group, a haloalkylsulfonyl group or an arylsulfonyl group, or
either $R^1$ groups or $R^2$ groups may be bonded at their terminals to form a ring; and
$R^3$ represents
an alkyl group optionally substituted with an alkoxy group, a phenoxy group, a dialkylamino group or a halogen atom,
an aralkyl group optionally substituted with an alkyl group, an alkoxy group, a phenoxy group, a nitro group or a halogen atom,
an aryl group optionally substituted with an alkyl group, an alkoxy group, a nitro group or a halogen atom.

The second aspect of the present invention relates to
a process for producing an optically active imidazolidin-2-one of formula (4):

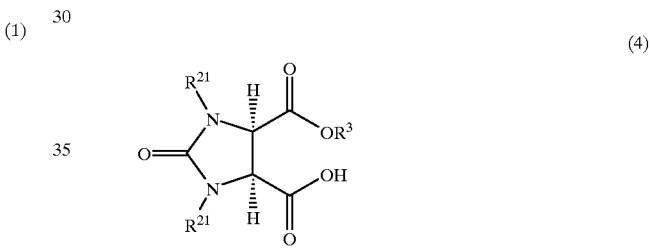

(4)

wherein $R^{21}$ represents the same as defined below and $R^3$ represent the same as defined above,
which comprises reacting a cyclic acid anhydride of formula (5):

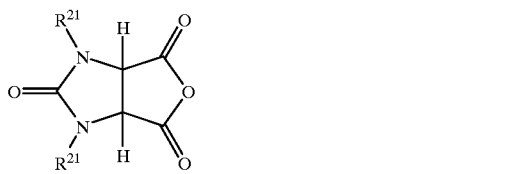

(5)

wherein $R^{21}$ represents
an alkyl group optionally substituted with an alkoxy group or a halogen atom,
an aralkyl group optionally substituted with an alkyl group, an alkoxy group or a halogen atom,
an aryl group optionally substituted with an alkyl group, an alkoxy group or a halogen atom, with a hydroxy compound of formula (3):

$R^3OH$ (3)

wherein $R^3$ is the same as defined above, in the presence of an optically active alkaloid selected from quinine, epiqunine, cinconine and cinconidine.

DETAILED DESCRIPTION

The first aspect of the present invention will be explained first. In the cyclic acid anhydride of formula (2), examples of the halogen atom represented by $R^1$ or $R^2$ include a fluorine atom, a chlorine atom, a bromine atom and an iodine atom, Examples of the alkyl group optionally substituted with an alkoxy group or a halogen atom represented by $R^1$ or $R^2$ include a linear, branched or cyclic alkyl group having 1 to 10 carbon atoms, which alkyl group may be optionally substituted with a halogen atom, an alkoxy group (e.g., a (C1–C5) alkoxy group such as methoxy, ethoxy, n-propoxy, or i-propoxy group, i-butoxy group, s-butoxy group, t-butoxy group, n-pentyloxy group, i-pentyloxy group, or neo-pentyloxy group) and the like.

Specific examples of the optionally substituted alkyl group include a methyl group, an ethyl group, a n-propyl group, a i-propyl group, a n-butyl group, a i-butyl group, a s-butyl group, a t-butyl group, a n-pentyl group, isoamyl group, a hexyl group, a heptyl group, an octyl group, a nonyl group, a decyl group, a cyclopentyl group, a cyclohexyl group, a cycloheptyl group, a chloromethyl group, a dichloromethyl group, a trichloromethyl group, a bromomethyl group, a 1-chloroethyl group, a 2-chloroethyl group, a 1,2-dichloroethyl group, a 2,2,2-tricliloroethyl group, a methoxymethyl group, a 2-metoxyethyl group and the like.

Examples of the alkenyl group optionally substituted with an alkoxy group or a halogen atom include a (C2–C3) alkenyl group optionally substituted with an (C1–C5)alkoxy group or a halogen atom, Specific examples thereof include a vinyl group, a propen-1-yl group, a propen-2-yl group, a 2-methylpropen-1-yl group, a 2,2-dichlorovinyl group, a 2,2-dibromovinyl gorup, a 2-methoxyvinyl group and the like.

Examples of the aralkyl group optionally substituted with an alkyl group, an alkoxy group or a halogen atom include a (C7–C11)aralkyl group optionally substituted with a (C1–C5)alkyl group (e.g., a methyl group, an ethyl group, n-propyl group, i-propyl group or n-butyl group, s-butyl group, t-butyl group, n-pentyl group, i-pentyl group, or neo-pentyl group), a (C1–C5)alkoxy group, or a halogen atom.

Specific examples thereof include a benzyl group, a 1-phenethyl group, a 2-phenethyl group, an α-naphthylmethyl group, a β-naphthylmethyl group and the like, of which aromatic rings may be optionally substituted with at least one group selected from the halogen atom, the alkoxy group or the alkyl group as described above.

Examples of the aryl group optionally substituted with an alkyl group, an alkoxy group or a halogen atom include a (C6–C18)aryl (e.g.,a phenyl, naphthyl, anthranyl or phenanthryl) group which may be optionally substituted with the halogen atom, the (C1–C5)alkyl or (C1–C5)alkoxy group as described above and the like.

Examples of the alkyl group, aralkyl group, silyl group, or acyl group represented by $R^a$ respectively include a (C1–C5)alkyl group such as a methyl group, an ethyl group, a propyl group, a n-butyl group, t-butyl group, a pentyl group or the like a (C7–C8)aralkyl group such as a benzyl group or a phenethyl group, a silyl group having three (C1–C4)alkyl groups such as a trimethylsilyl group, a t-butyldimethylsilyl group or the like, a (C2–C6)acyl group such as an acetyl group, a benzoyl group or the like.

Examples of the acyl group represented by $R^b$ include the same acyl groups as described above. Examples of the alkyl group in the alkoxycarbonyl group or alkylsulfonyl group, and examples of the aralkyl group in the aralkyloxycarbonyl group respectively include the same groups as defined above for $R^a$.

Specific examples of the aryl sulfonyl group include a p-toluenesulfonyl group, or the like. Specific examples of the alkylsulfonyl group include a methylsulfonyl group. Specific examples of the haloalkylsulfonyl group include a trifluoromethanesulfonyl group and the like.

Examples of the group formed by either $R^1$ groups or $R^2$ groups include a group of following formula (9):

$$-(CH_2)_n-, \qquad (9a)$$

wherein n is an integer of 2 to 4, $$=C(CH_3)_2, \qquad (9b)$$

$$-NR^{21}CON(R^{21})- \qquad (9c)$$

wherein $R^{21}$ represents the same as defined above in connection with formula (5), or

(9d)

wherein X represents
—O—, —CH=CH—, —CH$_2$—, or —(CH$_2$)$_2$—, and
Y represents —CH=CH— or —(CH$_2$)$_2$—.

Substituents represented by $R^{21}$ are explained below.

The alkyl group optionally substituted with an alkoxy group or a halogen atom include a linear, branched or cyclic (C1–C10)alkyl group optionally substituted with a halogen atom or a (C1–C6)alkoxy group.

The aralkyl group optionally substituted with an alkyl group, an alkoxy group or a halogen atom include a (C7–C11)aralkyl group optionally substituted with a halogen atom, a (C1–C5)alkoxy group or a (C1–C5)alkyl group (e.g, a benzyl group or the like).

The aryl group optionally substituted with an alkyl group, an alkoxy group or a halogen atom include a (C6–C18)aryl group optionally substituted with a halogen atom, a (C1–C5) alkyl group or a (C1–C5)alkoxyl group.

Preferred are the aralkyl group described above. Particularly preferred is a benzyl group.

In $R^1$ and $R^2$ groups, either $R^1$ or $R^2$ groups are preferably hydrogen atoms. The group formed by $R^1$ or $R^2$ groups of formula (9c) above is preferred.

Specific examples of the cyclic acid anhydride of formula (2) include
(3R, 4S)-dimethyl-3,4-dihydrofuran-2,5-dione,
3-oxabicyclo[3.2.0]heptan-2,4-dione,
2,4,5,6,3a,6a-hexahydro-2-oxapentalen-1,3-dione,
4,5,6,7,3a,7a-hexahydroisobenzofuran-1,3-dione,
6,6-dimethyl- -oxabicyclo[3.1.0]hexan-2,4-dione,
4,10-dioxatricyclo[5.2.1.0<2,6>]decan-3,5-dione,
4,10-dioxatricyclo[5.2.1.0<2,6>]dec-8-ene-3,5-dione,
4-oxatricyclo[5,2,1,0<2,6>]decan-3,5-dione,
4-oxatricyclo[5.2.1.0<2,6>]dec-8-ene-3,5-dione,
4-oxacyclo[5.2.2.0<2,6>]undecan-3,5-dione,
4-oxatricyclo[5.2.2.0<2,6>]undec-8-ene-3,5-dione, 4,6-bisbenzyl-2,4-6-3a,6a-pentahydro-4,6-diaza-2-oxapentalen-1,3,5-trione 4,6-dimethyl-2,4,6,3a,6a-pentahydro-4,6-diaza-2-oxapentalen-1,3,5-trione, 4,6-bisbenzyl-2,4,6,3a,6a-pentahydro-4,6-diaza-2-oxapentalen-1,3,5-trione, 4,6- diphenyl-2,4,6,3a,6a-pentahydro-4,6-diaza-2-oxapentalen-1,3,5-trione and the like. Anhydrides as described above are commercially available.

The $R^3$ group of the hydroxy compound of formula (3) will be explained below.

Examples of the alkyl group optionally substituted with an alkoxy group, a phenoxy group, a dialkylamino group or a halogen atom include a (C1–C8)alkyl group optionally substituted with a (C1–C5)alkoxy group, a phenoxy group, a di(C1–C3)alkylamino group, or a halogen atom.

Examples of the aralkyl group optionally substituted with an alkyl group, an alkoxy group, a phenoxy group, a nitro group or a halogen atom include a (C7–C8)aralkyl group (e.g, a benzyl group or a 1-, or 2-phenethyl group) optionally substituted with a (C1–C5)alkyl group, a (C1–C5)alkoxy group, a phenoxy group, a nitro group or a halogen atom.

Examples of the aryl group optionally substituted with an alkyl group, an alkoxy group, a nitro group or a halogen atom include a phenyl group optionally substituted with a (C1–C5)alkyl group, a (C1–C5)alkoxy group, a nitro group, or a halogen atom.

In the examples above, the (C1–C5)alkyl group or the (C1–C5)alkoxy group are the same as defined above for the substituent groups in $R^1$ and $R^2$.

Examples of the hydroxy compound of the formula (3) include an alkyl alcohol having said alkyl group as defined above, an aralkyl alcohol having said aralkyl group as defined above, an aryl alcohol having said aryl group as defined above and the like.

Specific examples thereof include methyl alcohol, ethyl alcohol, n-propyl alcohol, i-propyl alcohol, n-butyl alcohol, s-butyl alcohol, t-butyl alcohol, n-pentyl alcohol, neopentyl alcohol, amyl alcohol, hexyl alcohol, octyl alcohol, 2-methoxyethanol, 2-phenoxyethanol, 2- (dimethylamino) ethanol, 2-chloroethanol, benzyl alcohol, 2-methylbenzyl alcohol, 4-methylbenzyl alcohol, 2-methoxybenzyl alcohol, 4-methoxybenzyl alcohol, 2-phenoxybenzyl alcohol, 4-phenoxybenzyl alcohol, 4-nitrobenzyl alcohol, 4-cholorobenzyl alcohol, phenol, 2-methylphenol, 4-methylphenol, 2-methoxyphenol, 4-methoxyphenol, 4-nitrophenol, 4-chlorophenol and the like.

Among the $R^3$ of the hydroxy compound of formula (3), preferred are the alkyl group optionally substituted with an alkoxy group, a phenoxy group, a dialkylamino group or a halogen atom, and the aralkyl group optionally substituted with an alkyl group, an alkoxy group, a phenoxy group, a nitro group or a halogen atom.

More preferred are primary alcohols of formula $R^{33}CH_2OH$, wherein $R^{33}$ represents a (C1–C7)alkyl group optionally substituted with a (C1–C5)alkoxy group, a phenoxy group, a di(C1–C3) alkylamino group, or a halogen atom, or a phenyl group optionally substituted with a (C1–C5) alkyl group, a (C1–C5)alkoxy group, a phenoxy group, a nitro group, or a halogen atom.

An amount of the hydroxy compound (3) is not particularly limited, and the compound may be used, as a solvent, in excess to the cyclic acid anhydride (2), and may be recovered after completion of the reaction, for example, by distillation or the like. An amount of the hydroxy compound (3) is typically 1 mole or more per mol of the cyclic acid anhydride (2).

The asymmetric catalyst to be used in the present process can be prepared by contacting a Lewis acid compound selected from a halide, alkoxide or trifluoromethanesulfonate of an element of Group 3, 4, 13 or 14 of Periodic Table of the Elements with an optically active ligand selected from a diol, aminoalcohol and bisoxazolidine compound.

Examples of the Lewis acid compound selected from a halide, alkoxide or trifluoromethanesulfonate of an element of Group 3, 4, 13 or 14 of Periodic Table of the Elements include a boron halide such as boron trifluoride, boron trichloride, an aluminium halide or alkoxide such as aluminium trichloride, aluminium triisopropoxide or the like, a tatinium halide or alkoxide such as titanium tetrachloride, titanium tetraisopropoxide or the like, a tin halide such as tin tetrachloride, tin dichloride or the like, a lanthanum alkoxide such as lanthanum triisopropoxide or the like, and scandium triflate (trifluoromethanesulfonate) or the like. In particular, tin dichloride and titanium tetraisopropoxide are preferred.

Examples of the optically active ligand include
an optically active amino alcohol of formula (7):

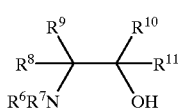

(7)

wherein $R^8$ and $R^9$ are different and $R^6$, $R^7$, $R^8$, $R^9$, $R^{10}$ and $R^{11}$ independently represent a hydrogen atom, an optionally substituted alkyl group, an optionally substituted alkenyl group, an optionally substituted aryl group, or $R^9$ and $R^{10}$ may be bonded to form an optionally substituted alkylene, and an optically active bisoxazolidine of formula (8):

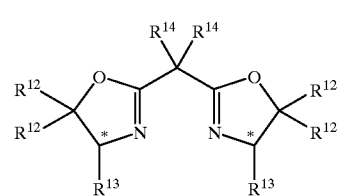

(8)

wherein $R^{12}$ represents a hydrogen atom, an optionally substituted alkyl group, or an optionally substituted aryl group, wherein two geminal alkyl groups may be bonded at their terminals to form a ring(e.g., an alkylene group), $R^{13}$ represents an optionally substituted alkyl group, an optionally substituted aryl group, and $R^{14}$ represents a hydrogen atom, an optionally substituted alkyl group, an optionally substituted aryl group, and the carbon atoms denoted by "*" represent asymmetric carbon atoms having an S or R configuration.

Examples of the optically active diol compound include optically active 1,1-binaphthol, 1,2-diphenylethan 1,2-diol and the like.

In $R^6$–$R^{11}$ of the optically active aminoalcohol of formula (7) will be explained below.

The optionally substituted alkyl group includes an alkyl group optionally substituted with an alkoxy group or a halogen atom (e.g., a linear, branched or cyclic alkyl group having 1 to 10 carbon atoms optionally substituted with a halogen atom, or a(C1–C5)alkoxy group), and an aralkyl group optionally substituted with an alkyl group, an alkoxy group or a halogen atom (e.g., a (C7–C11) aralkyl group optionally substituted with a (C1–C5)alkyl group, a (C1–C5)alkoxy group, or a halogen atom).

The optionally substituted alkenyl group includes an alkenyl group optionally substituted with an alkoxy group or a halogen atom(e.g., a (C2–C3)alkenyl group optionally substituted with an (C1–C5)alkoxy group or a halogen atom).

The optionally substituted aryl group includes an aryl group optionally substituted with an alkyl group, an alkoxy group or a halogen atom (a (C6–C18)aryl (e.g.,a phenyl, naphthyl, anthranyl or phenanthryl) group which may be optionally substituted with a halogen atom, a (C1–C5)alkyl or (C1–C5)alkoxy group).

Examples of the optionally substituted alkylene group include an ethylene or trimethylene group, which may be fused with a benzene ring (e.g., an indanyl group or the like).

With respect to the specific examples of these groups, those described above for $R^1$ and $R^2$ can be referred to.

In the optically active bisoxazoline of formula (8), the optionally substituted alkyl group, and the optionally substituted aryl group respectively have the same meaning as defined above in connection with formula (7).

Specific examples of the optically active ligand include optically active
1,1-binaphthol, 1,2-diphenylethan-1,2-diol,
2-amino-1,1-diphenyl-3-phenylpropan-1-ol, 1-amino-2-indanol,
2-amino-1-indanol, 2-amino 1,1-diphenyl-2-phenylethan-1-ol,
2-amino-1-diphenyl-3-methylbutan-1-ol,
2-amino-1,1-bis[2-butoxy-4-(2-methylpropan-2-yl)phenyl]-3-phenylpropan-1-ol,
2-amino-1,1-bis[2-butoxy-4-(2-methylpropan-2-yl)phenyl]-2-phenylethan-1-ol,
2-amino-1,1-bis[2-butoxy-4-(2-methylpropan-2-yl)phenyl]-3-methylbutan-1-ol,
2-aminocyclopentanol, 2-aminocyclohexanol,
2,2'-isopropylidenebis(4-t-butyl-2-oxazoline),
2,2'-isopropylidenebis(4-phenyl-2-oxazoline),
2,2'-methylenebis(4-pheuyl-2-oxazoline) and the like.

Preferred are optically active aminoalcohol and bisoxazoline, more preferred are 2-amino-1,1-bis[2-butoxy-4-(2-methylpropan-2-yl)-phenyl]-3-phenylpropan-1-ol and 2,2'-isopropylidenebis(4-t-butyl-2-oxazoline).

The optically active ligands are commercially available or the optically active oxazoline can be produced according to a reference such as EP895992A or the like.

An amount of the Lewis acid compound to be used is not particularly limited but it is usually catalytic amount, for example, around 0.00001 to less than 1 mole, preferably around 0.0001 to 0.5 mole per mol of the cyclic acid anhydride (2).

An amount of the optically active ligand is not particularly limited but it is usually around 1 to 10 moles, preferably around 1 to 2 moles per mol of the Lewis acid compound. Said asymmetric catalyst can be produced by a process comprising contacting said Lewis acid compound with said optically active ligand, and thus formed catalyst may be isolated prior to use, alternatively, said catalyst may be prepared in situ. For example, said process of contacting said Lewis acid compound with said optically active ligand may be conducted simultaneously in a reaction system of reacting the cyclic acid anhydride (2) with the alcohol compound (3).

The reacting of the cyclic acid anhydride (2) with an alcohol compound (3) may be carried out in the co-presence a base selected from an inorganic base or an aromatic tertiary amine compound.

Examples of the inorganic base include a carbonate or bicarbonate of an alkali metal and a carbonate of alkaline earth metal (e.g., lithium carbonate, potassium carbonate, sodium carbonate, lithium hydrogen carbonate, potassium hydrogen carbonate, sodium hydrogen carbonate, magnesium carbonate), and ammonium carbonate, and Examples of the aromatic tertiary amine compound include N-methylimidazole, a pyridine compound (e.g, a pyridine compound optionally substituted with an alkyl or a halogen atom such as pyridine, 2-methyl-5-ethylpyridine, 2,6-dichloropyridine, picoline or the like) and the like.

Preferred are a carbonate or bicarbonate of an alkali metal or a carbonate of alkaline earth metal such as sodium carbonate, sodium hydrogen carbonate, potassium hydrogen carbonate, or magnesium carbonate, and a pyridine compound such as 2,6-dichloropyridine.

An amount of the base to be used is not particularly limited but it is usually around 10 moles or less, preferably around 2 moles or less per mol of the cyclic acid anhydride (2).

The reaction of the cyclic acid anhydride (1) with the hydroxy compound (3) is usually conducted in an inert gas atmosphere such as argon, nitrogen and the like. The reaction may be performed under a normal, pressurized or reduced pressure.

The reaction may be performed without a solvent or in a solvent. Examples of the solvent to be used include a halogenated aliphatic hydrocarbon such as dichloromethane, chloroform, 1,2-dichloromethane and the like, an aliphatic hydrocarbon such as hexane, heptane, octane, nonane, or the like, an aromatic hydrocarbon such as benzene, toluene, xylene, a halogenated aromatic hydrocarbon such as chlorobenzene or the like, an ether solvent such as diethyl ether or tetrahydrofuran, and a mixed solvent thereof.

A reaction temperature is not particularly limited but it is usually in a range of −80 to 100° C., preferably −50 to 50° C.

After completion of the reaction, the catalyst can be removed from optically active hemiesters (3) by washing with water or acidic water and the product can be readily separated from the reaction mixture by usual post treatment such as extraction, phase separation, distillation or the like, and it may be further purified by column chromatography or the like, if necessary. The organic base may be recovered, for example, by adding a strong base to the separated aqueous phase.

Next, a description will be made to the second aspect of the present invention, which relates to a process for producing an optically active imidazolidin-2-one of formula (4), which comprises reacting a cyclic acid anhydride of formula (5) with a hydroxy compound of formula (3) in the presence of an optically active alkaloid selected from quinine, epiquinine, cinchonine and cinchonidine.

In formula (4) and (5), $R^{21}$ is the same as defined above in connection with formula (9c). $R^{21}$ is preferably the aralkyl group optionally substituted with an alkyl group, an alkoxy group or a halogen atom, and more preferably a benzyl group.

Examples of the cyclic acid anhydride of formula (5) include 4,6-dimethyl-2,4,6,3a,6a-pentahydro-4,6-diaza-2-oxapentalen-1,3,5-trione, 4,6-bisbenzyl-2,4,6,3a,6a-pentahydro-4,6-diaza-2-oxapentalen-1,3,5-trione, 4,6-diphenyl-2,4,6,3a,6a-pentahydro-4,6-diaza-2-oxapentalen-1,3,5-trione and the like.

Among the optically active alkaloid, quinine is preferred.

An amount of the optically active alkaloid to be used is not particularly limited and is usually around 0.00001 to 1 mole or may be catalytic amount, for example, less than 1 mol per mol of the cyclic acid anhydride (2).

The reaction is preferably carried out in the co-presence of a base, Examples of the base include an inorganic base (e.g., a carbonate or bicarbonate of an alkali metal or a carbonate of alkaline earth metal such as lithium carbonate, potassium carbonate, sodium carbonate, lithium hydrogen carbonate, potassium hydrogen carbonate, sodium hydrogen carbonate, magnesium carbonate or the like), and ammonium carbonate, and an aliphatic or aromatic tertiary amine compound such as trimethylamine, ethyldiisopropylamine, pyridine, 1,2,2,6,6-pentamethyl piperidine, 2-methyl-5-ethylpyridine, 2,6-dichloropyridine, picoline, N-methylimidazole and the like. In particular, 1,2,2,6,6-pentamethyl piperidine is preferred.

An amount of the base to be used is not particularly limited but is usually around 0.1 to 10 moles, preferably around 0.1 to 2 moles per mol of the cyclic acid anhydride (5).

The reaction of the cyclic acid anhydride (5) with the hydroxy compound (3) is conducted in the presence of the optically active alkaloid, and usually in an inert gas atmosphere such as argon, nitrogen and the like. The reaction may be performed either under a normal, pressurized or reduced pressure.

The reaction can be performed without a solvent or in a solvent. Examples of the solvent to be used include a halogenated hydrocarbon such as dichloromethane, chloroform, 1,2-dichloroethane, carbon tetrachloride and the like, an aliphatic hydrocarbon such as hexane, heptane, octane and nonane, an aromatic hydrocarbon such as benzene, toluene, xylene, or the like, a halogenated aromatic hydrocarbon such as chlorobenzene and the like, an ether solvent such as diethyl ether and tetrahydrofuran, and a mixed solvent thereof.

A reaction temperature is not particularly limited and is usually in a range of −80 to 100° C., preferably −60 to 50° C.

After completion of the reaction, the base can be removed from optically active imidazolidin-2-ones (4) by washing with water or acidic water. The desired product can be readily separated from the reaction mixture by a post-treatment such as extraction, phase separation, concentration and/or the like. The alkaloid and the aliphatic or aromatic tertiary amine compound may be recovered, for example, by adding a strong base to an aqueous phase obtained by washing the reaction mixture.

EXAMPLES

The present invention will be explained in more detail by way of Examples but is not limited to them.

Example 1

17.5 mg (0.01 mmol) of titanium tetraisopropoxide and 38.1 mg (0.06 mmol) of (R)-2-amino 1,1-bis[2-butoxy-4-methylpropan-2-yl]phenyl]-3-phenylpropan-1-ol were added in a 20 ml flask purged with nitrogen, and 5 ml of toluene was added thereto to dissolve them, and the resulting solution was cooled to 0° C. Then, 200 mg (0.6 mmol) of cis-4,6-bisbenzyl-2,4,6,3a,6a-pentahydro-4,6-diaza-2-oxapentalen-1,3,5-trione, 66 mg (0.6 mmol) of benzyl alcohol were added thereto in one portion or dropwise respectively, and the resulting reaction mixture was stirred at the same temperature for 13 hours.

2N hydrochloric acid was added to the reaction, and the product was extracted with diethyl ether. After the separated organic phase was washed with a saturated aqueous sodium chloride solution, it was analyzed by HPLC (internal standard: diisopropyl phthalate). (4R, 5S)-1,3-bisbenzyl-2-oxo-5-[benzyloxycarbonyl]imidazolidin- 4-carboxylic acid was obtained in a yield of 43.2%, and the optical purity was measured with an optically active HPLC column (manufactured by Sumika Chemical Analysis Service: SUMICHIRAL OA-3300) and found to be 23.7% ee.

Example 2

17.5 mg (0.06 mmol) of titanium tetraisopropoxide and 38.1 mg (0.06 mmol) of (R)-2-amino-1,1-bis[2-butoxy-4-methylpropan-2-yl]phenyl]-3-phenylpropan-1-ol were added to a 20 ml flask purged with nitrogen, and 5 ml of toluene was added thereto to dissolve them, and cooled to 0° C. Then, 200 mg (0.6 mmol) of cis-4,6-bisbenzyl-2,4,6,3a, 6a-pentahydro-4,6-diaza-2-oxapentalen-1,3,5-trione, 66 mg (0.6 mmol) of benzyl alcohol, and 64.4 mg (0.6 mmol) of sodium carbonate were added thereto, and the resulting mixture was stirred at the same temperature for 13 hours.

Post-treatment and analysis were performed as in Example 1. (4R, 5S)-1,3-bisbenzyl-2-oxo-5-[benzyloxycarbonyl]imidazolidin-4-carboxylic acid was obtained in a yield of 78.7% and the optical purity was 50.6% ee.

Examples 3–9

(4R, 5S)-1,3-bisbenzyl-2-oxo-5-[benzyloxycarbonyl] imidazolidin-4-carboxylic acid was obtained in a similar manner as in Example 2 except that a base shown in Table 1 was used instead of sodium carbonate in Example 2. The results are shown in Table 1.

TABLE 1

| | | Product | |
| --- | --- | --- | --- |
| Example | Base | Yield % | Optical purity/% ee |
| 3 | Pyridine | 73.6 | 38.5 |
| 4 | 2-methyl-5-ethylpyridine | 72.1 | 26.0 |
| 5 | N-methylimidazole | 65.4 | 7.5 |
| 6 | 2,6-dichloropyridine | 63.4 | 50.2 |
| 7 | Sodium hydrogen carbonate | 75.5 | 50.4 |
| 8 | Potassium hydrogen carbonate | 76.2 | 49.0 |
| 9 | Magnesium carbonate | 72.3 | 49.8 |

Example 10

11.1 mg (0.06 mmol) of tin chloride(II) and 18 mg (0.06 mmol) of 2,2'-isopropylidenebis((4S)-4-t-butyl-2-oxazoline) were added to a 20 ml of flask purged with nitrogen, and 5 ml of toluene was added thereto to dissolve them, and cooled to 0° C. Then, 200 mg (0.6 mmol) of cis-4,6-bisbenzyl-2,4,6,3a,6a-pentahydro-4,6-diaza-2-oxapentalen-1,3,5-trione, 61.9 mg (0.6 mmol) of benzyl alcohol were respectively added thereto in one portion or dropwise, and the resulting mixture was stirred at the same temperature for 13 hours.

Post-treatment and analysis were performed as in Example 1. (4R, 5S)-1,3-disbenzyl-2-oxo-5-[benzyloxycarbonyl]imidazolidin-4-carboxylic acid was obtained in a yield of 39.94% and the optical purity was 55.2% ee.

Example 11

199 mg (0.06 mmol) of cis-4,6-bisbenzyl-2,4,6,3a,6a-pentahydro-4,6-diaza-2-oxapentalen-1,3,5-trione was added to a 20 ml flask purged with nitrogen, and 5 ml of toluene was added thereto and cooled to −50° C. Then, 212.7 mg (0.06 mmol) of quinine, 53.1 mg (1.7 mmol) of methanol was respectively added in one portion or dropwise, and the resulting mixture was stirred at the same temperature for 21 hours. 2N hydrochloric acid was added to the reaction mixture to stop the reaction, and the product was extracted with diethyl ether. The separated organic phase was washed with a saturated aqueous sodium chloride solution, and subjected to quantitative analysis by HPLC (internal standard: diisopropyl phthalate). (4S, 5R)-1,3-bisbenzyl-2-oxo-5-(methoxycarbonyl)imidazolidin-4-carboxylic acid was obtained in a yield of 49.1%, The optical purity was measured with an optically active HPLC column (manufactured by Sumika Chemical Analysis Service: SUMICHIRAL OA-3300) and found to be 73.3% ee.

Example 12

199 mg (0.6 mmol) of cis-4,6-bisbenzyl-2,6,6,3a,6a-pentahydro-4,6-diaza-2-oxapentalen-1,3,5-trione was placed in a 20 ml flask purged with nitrogen, and 2.5 ml of toluene and 2–5 ml of carbon tetrachloride were added thereto. The resulting solution was cooled to −20° C. Then, 213.9 mg (0.06 mmol) of quinine, 64.0 mg (0.6 mmol) of benzyl alcohol were respectively added in one portion or dropwise, and the resulting solution was stirred at the same temperature for 16 hours. Thereafter, the reaction mixture was treated as in Example 11. (4S, 5R) -1,3-bisbenzyl-2-oxo-5-(methoxycarbonyl)imidazolidin-4-carboxylic acid was obtained in a yield of 76.8%. The optical purity of the product was 73.6% ee.

Example 13

According to the same manner as that in Example 12 except that cinchonidine was used instead of quinine in Example 12, (4S, 5R)-1,3-bisbenzyl-2-oxo-5-(methoxycarbonyl)imidazolidin-4-carboxylic acid was obtained in a yield of 81.4%, The optical purity of the product was 25.9% ee.

Example 14

202 mg (0.69 mmol) of cis-4,6-bisbenzyl-2,6,6,3a,6a-pentahydro-4,6-diaza-2-oxapentalen-1,3,5-trione was added in a 20 ml flask purged with nitrogen, and 5 ml of toluene was added thereto, and the resulting solution was cooled to −50° C. Then, 19.3 mg (0.06 mmol) of quinine and 106.0 mg (0.68 mmol) of 1,2,2,6,6-pentamethyl piperidine were added thereto, and 55.0 mg (1.7 mmol of ethanol was added dropwise thereafter, and the resulting solution was stirred at the same temperature for 21 hours. The reaction mixture was treated as in Example 11. (4S, 5R)-1,3-bisbenzyl-2-oxo-5-(methoxycarbonyl)imidazolidin-4-carboxylic acid was obtained in a yield of 56.0%. The optical purity of the product was 59.8% ee.

What is claimed is:

1. A process for producing an optically active imidazolidin-2-one of formula (4):

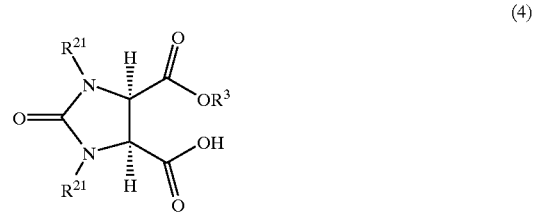

(4)

wherein $R^{21}$ and $R^3$ represents the same meanings as described below, which comprises reacting a cyclic acid anhydride of formula (5):

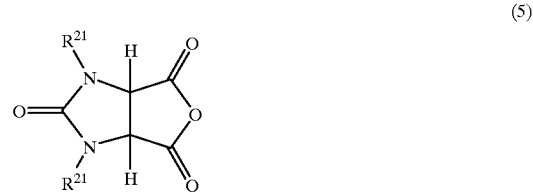

(5)

wherein $R^{21}$ represents
an alkyl group optionally subtituted with an alkoxy group or a halogen atom,
an aralkyl group optionally substituted with an alkyl group, an alkoxy group or a halogen atom,
an aryl group optionally substituted with an alkyl group, an alkoxy group or a halogen atom, with a hydroxy compound of formula (3):

$R^3OH$ (3)

wherein $R^3$ represnts
an alkyl group optionally substituted with an alkoxy group, a phenoxy group, a dialkylamino group or a halogen atom,
an aralkyl group optionally substituted with an alkyl group, an alkoxy group, a phenoxy group, a nitro group or a halogen atom,
an aryl group optionally substituted with an alkyl group, an alkoxy group, a nitro group or a halogen atom, in the presence of a catalytic amount of an optically active alkaloid selected from quinine, epiqunine, cinconine and cinconidine.

2. The process according to claim 1, wherein $R^{21}$ represents
a linear, branched or cyclic (C1–C10)alkyl group optionally substituted with a halogen atom or a (C1–C5) alkoxy group,
a (C7–C11)aralkyl group optionally substituted with a halogen atom or a (C1–C5)alkyl group or
a (C6–C18)aryl group optionally substituted with a halogen atom or a (C1–C5)alkyl group, $R^2$ represents
- a (C1–C8)alkyl group optionally substituted with a (C1–C5)alkoxy group, a phenoxy group, a di(C1–C3) alkylamino group or a halogen atom,
- a benzyl group optionally substituted with a (C1–C5)alkyl group, a (C1–C5)alkoxy group, a phenoxy group, a nitro group or a halogen atom, or
- a phenyl group optionally substituted with a (C1–C5) alkyl group, a (C1–C5)alkoxy group, a nitro group or a halogen atom, and $R^3$ represents
- a (C1–C8)alkyl group optionally substituted with a (C1–C5)alkoxy group, a phenoxy group, a di(C1–C3) alkylamino group, or a halogen atom,
- a (C7–C8)aralkyl group optionally substituted with a (C1–C5)alkyl group, a (C1–C5)alkoxy group, a phenoxy group, a nitro group or a halogen atom, or
- a phenyl group optionally substituted with a (C1–C5) alkyl group, a (C1–C5)alkoxy group, a nitro group or a halogen atom.

3. The process according to claim 1 or 2, wherein reacting of said cyclic acid anhydride of formula (5) with said hydroxy compound of formula (3) is conducted in the presence of said optically active alkaloid compound and a base.

4. The process according to claim 1, wherein $R^{21}$ is an aralkyl group optionally substituted with an alkyl group, an alkoxy group or a halogen atom.

5. The process according to claim 2, wherein $R^{21}$ is a benzyl group.

6. The process according to claim 5, wherein said alkaloid is quinine.

7. The process according to claim 3, wherein said base is an aliphatic or aromatic tertiary amine.

8. The process according to claim 3, wherein said base is a piperidine compound.

* * * * *